United States Patent [19]

Nonaka et al.

[11] Patent Number: 5,008,620
[45] Date of Patent: Apr. 16, 1991

[54] LEAKAGE FLUX FLAW DETECTION METHOD AND APPARATUS UTILIZING A LAYERED DETECTOR

[75] Inventors: Katusnobu Nonaka, Tsuchiura; Kazuyoshi Sekine, Yokohama, both of Japan

[73] Assignees: Agency of Industrial Science & Technology; Ministry of International Trade & Industry, both of Tokyo, Japan

[21] Appl. No.: 489,235

[22] Filed: Mar. 6, 1990

[30] Foreign Application Priority Data

Mar. 10, 1989 [JP] Japan ................................. 1-58478

[51] Int. Cl.⁵ ..................... G01N 27/82; G01R 33/12
[52] U.S. Cl. .................................................. 324/213
[58] Field of Search ..................... 324/213; 347/74.2; 360/134; 252/62.52

[56] References Cited

U.S. PATENT DOCUMENTS

3,845,382 10/1974 Forster .............................. 324/213

Primary Examiner—Walter E. Snow
Attorney, Agent, or Firm—Oblon, Spivak, McClelland, Maier & Neustadt

[57] ABSTRACT

A leakage flux flaw detection method and apparatus comprising applying one surface of a magnetic recording material to the test surface of a test material and overlaying the other surface of the magnetic recording material with a layer of magnetic material with the intervention of a non-magnetic layer, and the use of a magnetizer and an auxiliary recording member provided with layers of magnetic and non-magnetic materials.

13 Claims, 8 Drawing Sheets

LEAKAGE FLUX FLAW DETECTION METHOD AND APPARATUS UTILIZING A LAYERED DETECTOR

BACKGROUND OF THE INVENTION

1. Field of the Invention

This invention relates to a leakage flux flaw detection method and apparatus for detecting flaws in ferromagnetic materials such as alloys containing iron, cobalt or nickel, for example, by magnetizing the ferromagnetic material and utilizing magnetic flux leakage from a flaw portion to detect flaws.

2. Prior Art Statement

Magnetic flaw testing is a non-destructive method of testing for flaws in ferromagnetic materials such as alloys of iron, cobalt or nickel.

Leakage flux flaw detection is a typical example of a magnetic flaw test method in which a test material is magnetized and flaws are detected by detecting flux leakage from the flawed portion, and which is used in magnaflux flaw detection and magnetic recording flaw detection.

Figure 1A:
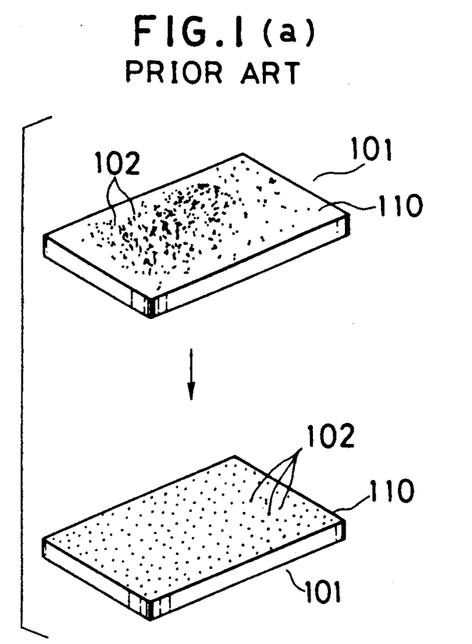

The conventional magnaflux flaw detection method will now be described with reference to FIG. 1. When magnetic powder 102, such as iron particles, for example, is scattered on the test surface 110 of a test material 101 that is magnetized using a magnetizer or the like, the magnetic powder 102 will adhere to the test surface 110 of the test material 101 if the test surface 110 or surface layer portion of the test material 101 is free of flaws, since the strength of the magnetic field will be the same over the whole surface portion of the material and there is no leakage of magnetic flux (FIG. 1 (a)).

Figure 1B:
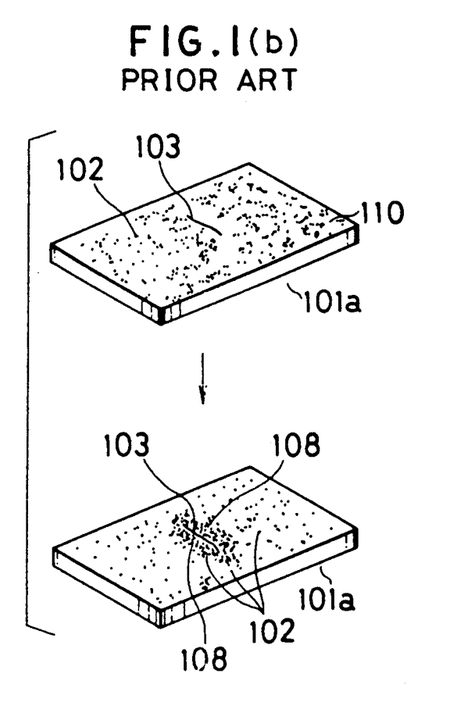
Figure 2:
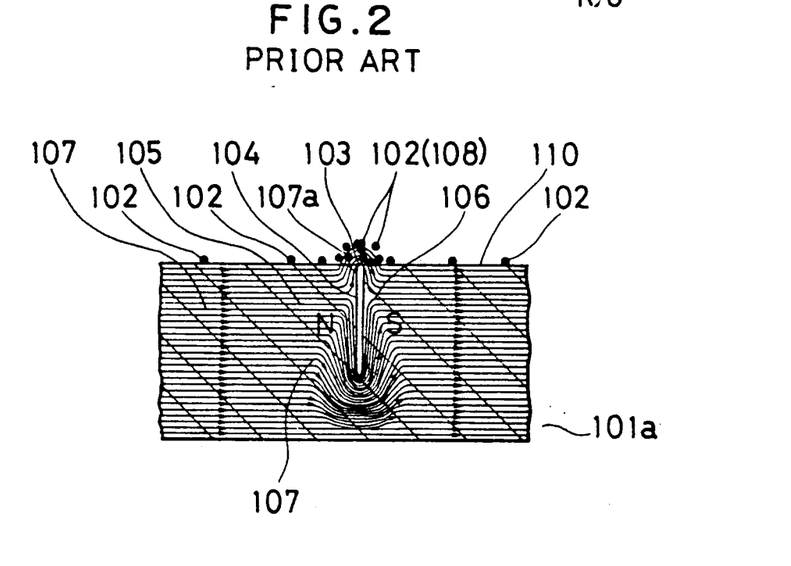
FIG. 2 is a cross-sectional view of the portion of the material shown in FIG. 1 (b) which contains the magnetic powder pattern.

However, when the material has a flaw such as the flaw 103 in the material 101a shown in FIG. 2, an electric field is formed across the groove 104 of the flaw 103, with the wall 105 at one side of the groove forming the negative pole and the wall 106 at the other side forming the positive pole, and part of the magnetic flux 107 that connects the two sides forms a leakage magnetic flux 107a from the test surface 110 of the material 101a. This causes a concentration of the magnetic powder 102 along the lines of leakage flux around the flaw 103 portion, forming a magnetic powder pattern 108 on the test surface 110 (FIG. 1 (b)). Thus, the shape and extent of a flaw such as the flaw 103, and its depth, is estimated by the presence or absence of such a magnetic powder pattern 108, and the shape, size and height of the pattern.

A feature of the magnaflux flaw detection method is that it does not require elaborate equipment and can be readily carried out by anyone. The method has a number of drawbacks, however. For example, the method involves a manual operation and therefore cannot be carried out unattended and the results depend on the technical proficiency of the person performing the examination, very small flaws are often overlooked owing to the equivocal nature of the magnetic powder pattern and the fact that recording it is not possible; and objective, quantitative evaluations and evaluations based on changes over time are also difficult.

Figure 3A:
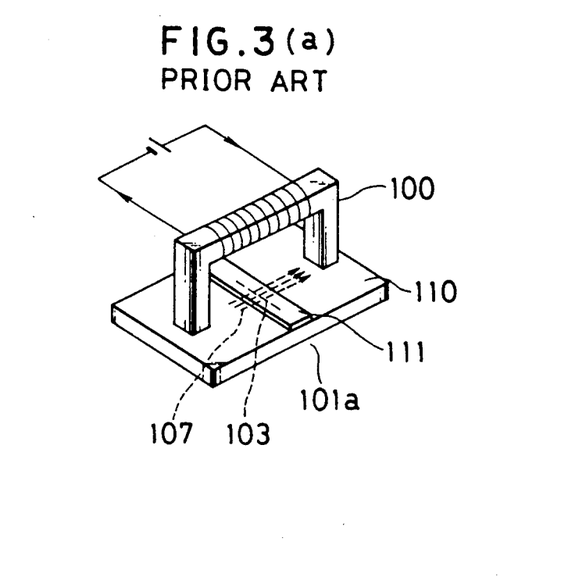
Figure 3B:
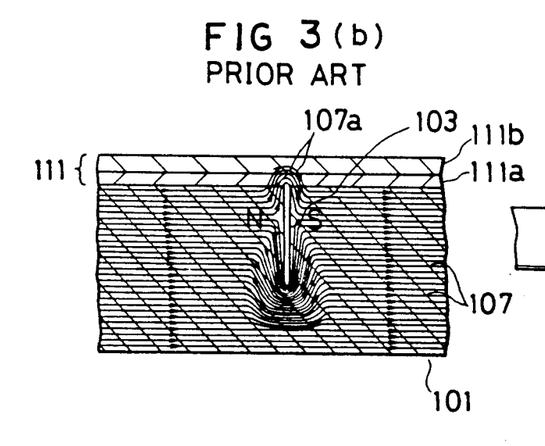
Figure 3C:
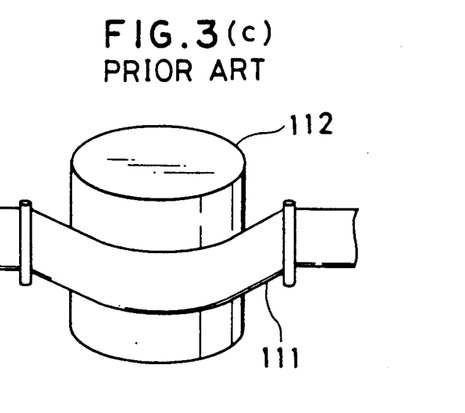

In the conventional magnetic recording flaw detection method, the magnetic head has a large gap and, as shown in FIG. 3, with the magnetic tape 111 or other such recording medium laid on the test surface 110 of the test material 101, the material 101a is magnetized by means of the magnetizer 100 (FIG. 3 (a)) and leakage flux 107a from the flaw 103 portion of the material 101a is recorded on the magnetic layer 111a of the magnetic tape 111. Thus the degree of magnetization of the portion of the magnetic layer 111a through which the leakage flux 107a passes is made to correspond to the general direction of the leakage flux 107a (FIG. 3 (b)), and after the recording the magnetic tape 111 is run past magnetic head 112 to convert the magnetization orientation and intensity to corresponding induction voltages (FIG. 3 (c)) and the voltage signal waveform thus obtained is analyzed to evaluate the flaw 103.

Since the magnetic recording flaw detection method can be automated it can be performed unattended, and the ability to make a recording makes it possible to make objective, quantitative evaluations and evaluations of changes over time.

However, a problem with the conventional magnetic recording flaw detection method is that the magnetic recording head has a large gap and the magnetic force of the leakage flux 107a with respect to the magnetic layer 111a is small, so that the leakage flux 107a is not clearly recorded on the magnetic tape 111. At even a minute distance from the test surface 110 there is a rapid attenuation of the leakage flux 107a, so it is therefore necessary to keep the magnetic tape 111 lift-off as small as possible. Means of achieving this include placing a rubber sheet on the magnetic tape 111, but when a flaw is very small or the material is very thin or is coated, the signals obtained may be so weak as to be indistinguishable from noise, in which case it is, for practical purposes, impossible to conduct the test.

There are other magnetic flaw detection methods. However, if a magnetic sensor is used the lift-off produced by the thickness of the sensor also makes it difficult to detect small flaws and flaws in thin or coated materials.

OBJECT AND SUMMARY OF THE INVENTION

An object of this invention is therefore to provide a leakage flux flaw detection method and apparatus whereby tests can be performed automatically and recorded, and objective, quantitative evaluations and time-lapse evaluations can be carried out and applied to the detection of small flaws and flaws in thin and coated materials.

For attaining the aforesaid object, the leakage flux flaw detection method according to the present invention comprises applying one surface of a magnetic recording material to the test surface of a test material and overlaying the other surface of the magnetic recording material with a layer of magnetic material with the intervention of a non-magnetic layer, forming a magnetic path that passes through the test material.

The leakage flux flaw detection apparatus comprises a magnetizer and an auxiliary recording member, the auxiliary recording member being provided with a layer of magnetic material and a layer of non-magnetic material, with the magnetic layer separated from the magnetic recording material by the non-magnetic layer.

Thus, since, as described above, in accordance with this invention one surface of the magnetic recording material is placed in contact with a surface of the test material and a layer of magnetic material is placed in contact with the other surface with the intervention of a non-magnetic layer, forming a magnetic path which facilitates and increases the flow of the leakage flux, so that the layer of magnetic material itself is magnetized by the leakage flux, thereby increasing the magnetization of the magnetic recording material.

The result is that it becomes possible to accomplish reliably the detection of flaws which previously have been undetectable owing to the low intensity of the leakage flux and the inability to make a recording. That is, with this invention it is possible to record leakage flux from shallow flaws, narrow flaws, flaws in material where there is a large lift-off owing to the presence of a coating, and flaws in thin materials to which it is difficult to impart a strong magnetism, thereby enabling such flaws to be detected.

These and other objects and features of this invention will be better understood from the following detailed description made with reference to the drawings.

BRIEF DESCRIPTION OF THE DRAWINGS

FIG. 1 (a) illustrates a conventional magnaflux flaw detection method in which the test material has no flaws;

FIG. 1 (b) illustrates a conventional magnaflux flaw detection method in which the test material has a flaw;

FIG. 3 (a) illustrates a conventional leakage flux flaw detection method;

FIG. 3 (b) is a cross-sectional view illustrating the relationship between the flaw portion and the magnetic flux;

FIG. 3 (c) illustrates the use of a magnetic head to reproduce the flaw state from the magnetic recording material;

FIG. 4 (a) is a perspective view of the auxiliary recording member overlaid on the test material during leakage flux flaw detection;

FIG. 4 (b) is a perspective view illustrating the formation of a magnetic path through the test material;

FIG. 4 (c) is a cross-sectional view illustrating the relationship between the flaw portion and the magnetic flux;

DESCRIPTION OF THE PREFERRED EMBODIMENTS

Figure 4A:
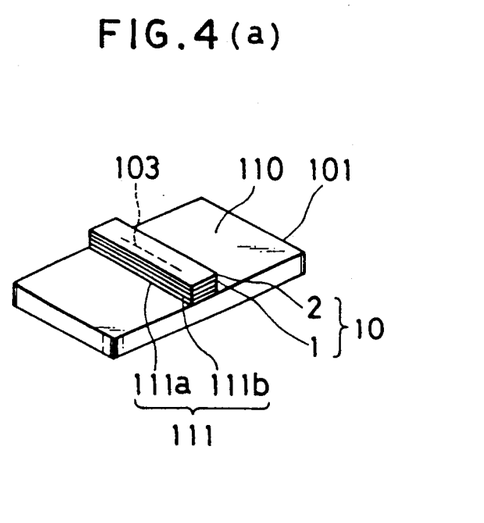

FIG. 4 shows a first embodiment of the leakage flux flaw detection method according to this invention. With reference to the drawing, a magnetic layer 111a of a magnetic tape 111, constituted of the magnetic layer 111a and a non-magnetic base film base film 111b, is arranged on a test surface 110 of a test material 101. Commercial magnetic tape may be used for the magnetic tape 111. A non-magnetic layer 1 is then placed on the base film 111b of the magnetic tape 111, and a ferromagnetic layer 2 is then placed on the non-magnetic layer 1 (FIG. 4 (a)).

A flexible high polymer material such as 0.2 -mm vinyl chloride may be used for the non-magnetic layer 1 and a ferromagnetic metal sheet material such as iron, or a magnetic high polymer, may be used for the ferromagnetic layer 2. Alternatively, the two layers, non-magnetic layer 1 and ferromagnetic layer, 2 may instead be formed as one integral layer. If the ferromagnetic layer 2 is a magnetic high polymer sheet, adherence between the magnetic tape 111 and the test surface 110 is enhanced.

Figure 4B:
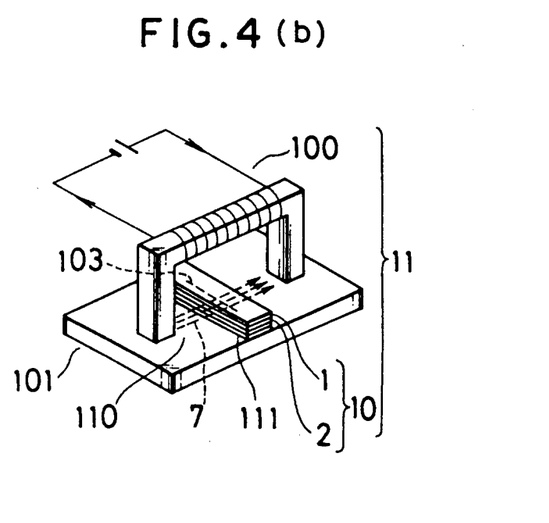
Figure 4C:
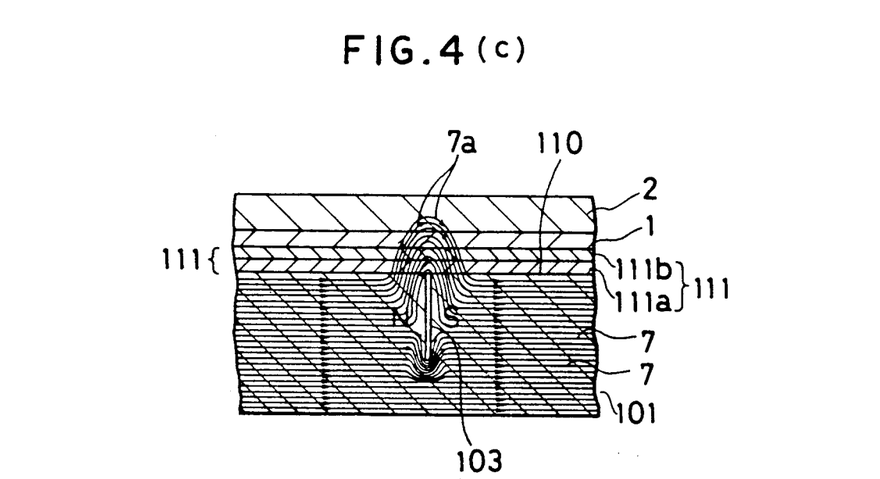

Thus, one surface of the magnetic layer 111a of the magnetic tape 111 is laid on the test surface 110 of the test material 101 and the other surface is overlaid by the non-magnetic layer 1 followed by the ferromagnetic layer 2, so there is zero lift-off of the magnetic tape 111 from the test material 101. The magnetic layer 111a is therefore in close contact with the test surface 110. The arrangement thus configured is magnetized by the magnetizer 100 (FIG. 4 (b)) to produce a flow of magnetic flux 7 in the test material 101 and a leakage flux 7a from the flaw 103 portion which is recorded on the magnetic layer 111a of the magnetic tape 111 (FIG. 4 (c)).

Figure 5:
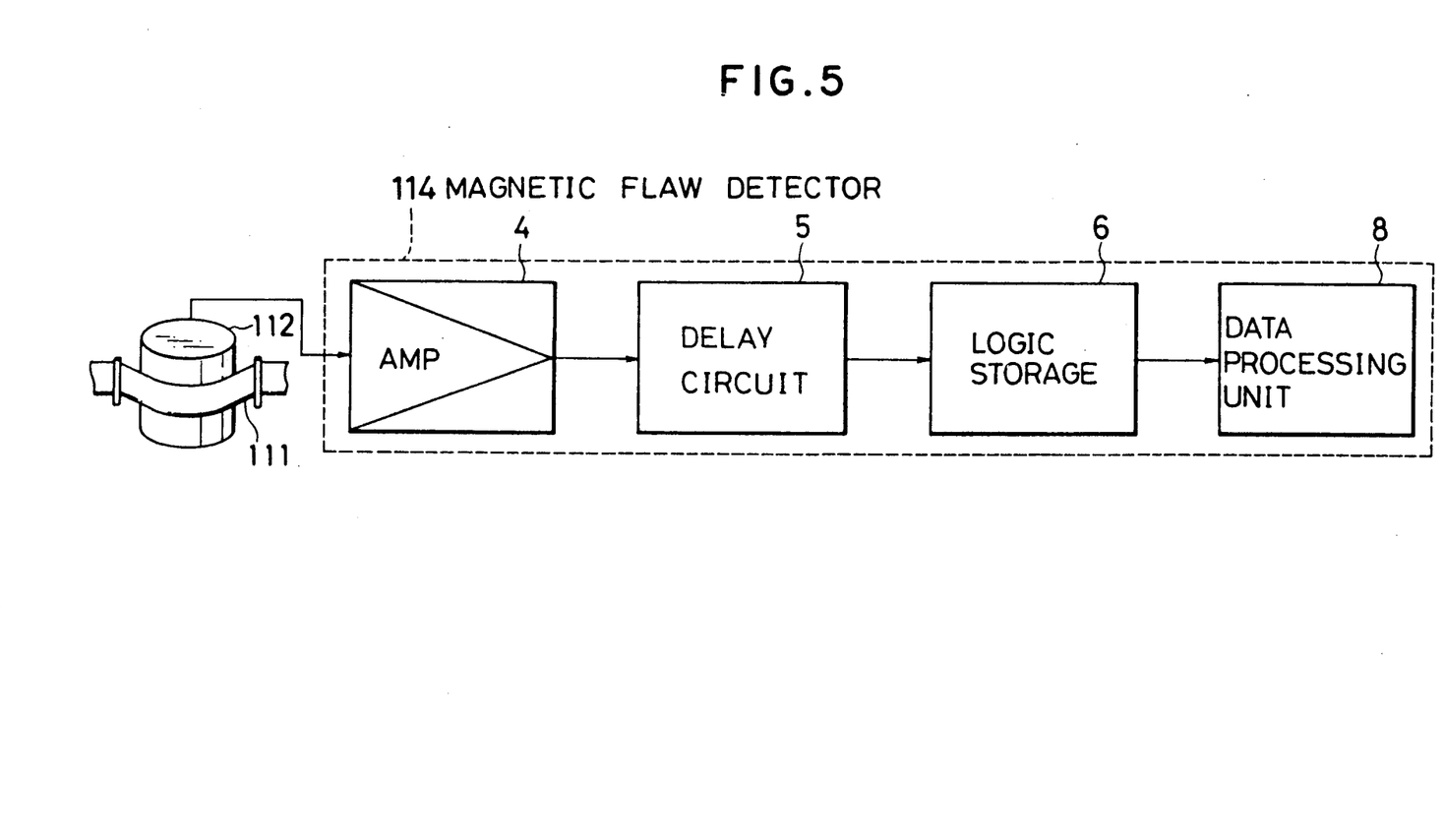
FIG. 5 is a block diagram of a magnetic recording apparatus for analyzing the waveform of the reproduced signal.

The magnetic tape 111 is then passed across a magnetic head 112, thereby inducing a potential in the magnetic coil of the magnetic head 112 which corresponds to the strength of the magnetic field set up by the leakage flux 7a, and this potential is used to obtain a signal waveform. A videotape or audio-tape recording head may be used for this magnetic head. The signal thus obtained is amplified by an amplifier 4 of a magnetic flaw detector 114 connected to the magnetic head 112, delayed by a delay circuit 5, stored in a logic storage 6, analyzed by a DPU (data processing unit) 8 and recorded/displayed as required (FIG. 5).

In this embodiment, the test material is a sheet that is thick enough to have a cross-sectional area large enough for a sufficient flow of flux and the material is magnetized directly by means of a magnetizer. If the material is very thin, however, and has a relatively low permeability, such as iron-system amorphous material 0.01 to 0.05 mm thick, such direct magnetization will not produce a sufficient flow of flux in the test material 101, and because flaws in such a material will necessarily be extremely shallow, the signal derived from the leakage flux may be too weak to use for flaw detection.

Figure 6:
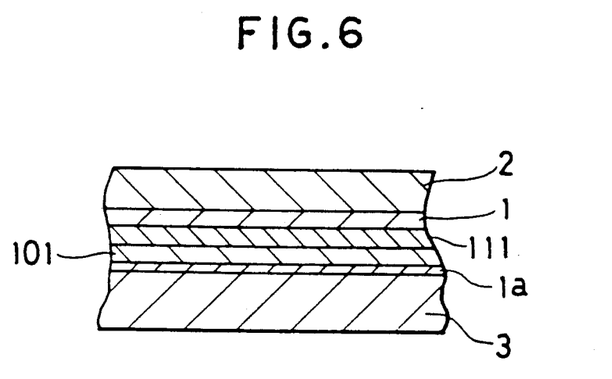
FIG. 6 is a cross-sectional view illustrating flaw detection when the test material is very thin sheet.

In such a case the arrangement shown in FIG. 6 can be used for the magnetization. Here, the thin test material 101 is arranged on a flat, flaw-free ferromagnetic material (such as sheet steel) 3 with a non-magnetic thin film 1a between the two, and in this state the ferromagnetic material 3 is magnetized, which enables the test material 101 to be magnetized more strongly than if it were magnetized on its own. The result is that a strong signal is obtained and the thin film 1a layer provides a separation from noise from the ferromagnetic material 3. The ferromagnetic layer 3 and the thin film 1a may be constituted of the same respective materials used for the ferromagnetic layer 2 and non-magnetic layer 1.

Figure 7:
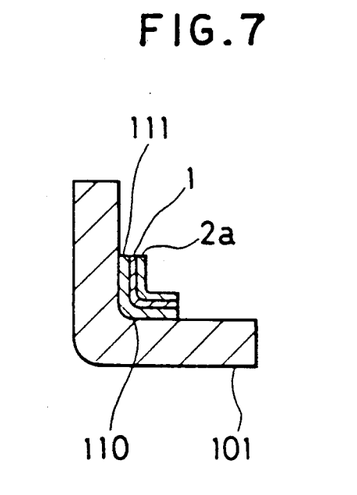
FIG. 7 is a cross-sectional view illustrating flaw detection when the test surface is curved.

FIG. 7 shows an arrangement that may be used when the test material has a curved surface. Here the magnetic tape 111 is arranged on the test material 101 so that it follows the contours of the test surface, and the magnetic tape 111 is overlaid by a non-magnetic layer 1 which in turn is overlaid by a ferromagnetic layer 2. The test material 101 is then magnetized with the three layers thus arranged in close mutual contact on the test surface 110 of the test material 101.

The leakage flux flaw detection apparatus will now be described. With reference to FIG. 4 (b), a leakage flux flaw detection apparatus 11 is provided with a magnetizer 100 and an auxiliary recording member 10. A commercial magnetizer may be used for the magnetizer 100.

The auxiliary recording member 10 may be formed as two separable layers such as the non-magnetic layer 1 and ferromagnetic layer 2 or can be formed as a single integrated member, and is arranged so that the ferromagnetic layer 2 is bonded to the magnetic tape or other such magnetic tape 111 via the non-magnetic layer 1.

The leakage flux flaw detection apparatus 11 is provided with a magnetic head 112 for converting leakage flux recorded in the magnetic tape 111 to electrical signals and a magnetic flaw detector 114 for processing the signals.

In the leakage flux flaw detection apparatus 11 configured as described above, detection of flaws in the test material 101 is implemented by bringing the magnetic tape 111 into close contact with the test surface 110 of the test material 101, then placing the auxiliary recording member 10 on the magnetic tape 111 so that the ferromagnetic layer 2 is in contact with the magnetic tape 111. This produces a pressure bond between the magnetic tape 111 and the test surface 110.

The magnetizer 100 is then positioned across the auxiliary recording member 10 and magnetization is carried out by energizing the magnetizer 100 while moving it lengthwise along the auxiliary recording member 10, producing a flow of flux in the test material 101, and leakage flux being recorded on the magnetic tape 111.

When one recording is completed, a blank portion of the recording material, with the auxiliary recording member 10, is moved to a part of the sample which has not yet been tested and the same sequence of magnetization and recording of leakage flux is repeated.

When recordings have been obtained of the prescribed areas of the test material the magnetic head 112 converts the magnetic flux information on the magnetic tape 111 into an electrical signal that has an amplitude which corresponds to the intensity of the leakage flux. These signals are then sent to the magnetic flaw detector 114 where they are processed to determine the existence and extent of any flaws.

The flaw detection can be automated by using a magnetic recording material formed into a strip that can be wound after each recording and the test material moved to bring the next area to be tested into position.

Figure 8:
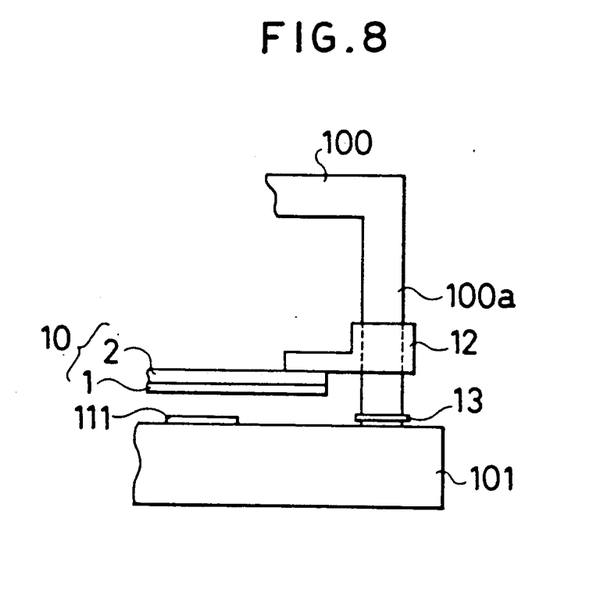
FIG. 8 shows the auxiliary recording member supported on the magnetizer ready for leakage flux flaw detection.

In the above embodiment, the auxiliary recording member 10 is formed separately from the magnetizer 100. However, a configuration such as the one shown in FIG. 8 may be used in which the auxiliary recording member 10 is supported on the magnetizer 100 by attaching the ferromagnetic layer 2 and the non-magnetic layer 1 to a support member 12 provided on the upright 100a of the magnetizer 100. In this arrangement, the auxiliary recording member 10 is insulated from the core of the magnetizer 100, and when the test sample 101 is to be tested the support member 12 is lowered to bring the auxiliary recording member 10 into contact with the magnetic tape 111 on the test sample 101 and the magnetizer 100 or test sample 101 is moved and leakage flux from the test sample 101 is recorded on the magnetic tape 111. A stop 13 is provided to prevent the support member 12 coming off the upright 100a.

The invention will now be explained with respect to examples but is not limited to these examples.

Steel sheet (SM 50) measuring 45 mm by 200 mm by 20 mm thick was used as the test material. Three grooves were formed in the material, measuring respectively 1.15 mm, 0.2 mm and 0.008 mm in depth. Commercial magnetic tape was placed on the test material and was overlaid with a sheet of non-magnetic material 0.2 mm thick constituted of vinyl chloride, which is further overlaid with a magnetic layer constituted by a steel sheet measuring 60 mm by 80 mm by 0.2 mm thick. This was followed by magnetization of the test material at a magnetization current of 10 amps in a magnetizer (model UM-3ME manufactured by Denshi Jiki Industry Co., Ltd.) and the recording of the leakage flux from each flaw (groove).

Figure 9:
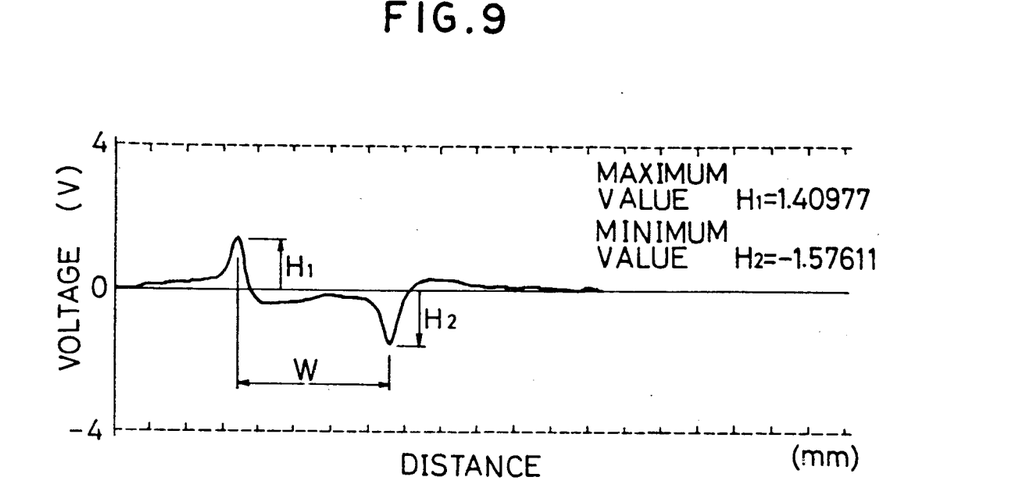
FIG. 9 is a graph of a signal waveform obtained from a 1.5 -mm-deep groove in the test material using the method according to the present invention.
Figure 10:
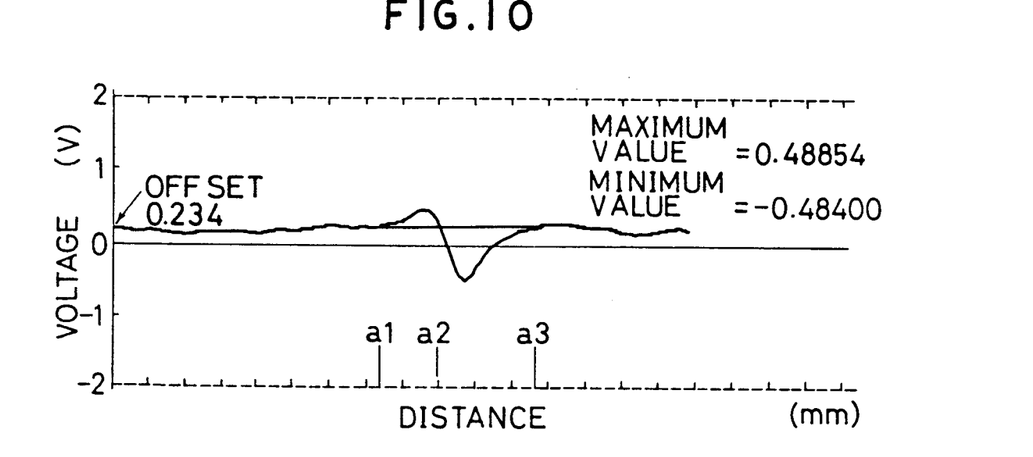
FIG. 10 is a graph of a signal waveform obtained from a 1.2 -mm-deep groove in the test material using the method according to the present invention.
Figure 11:
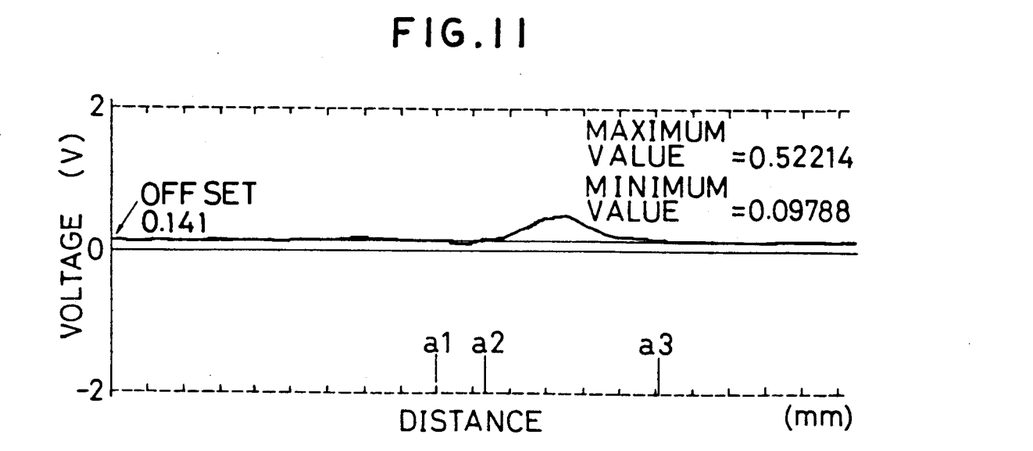
FIG. 11 is a graph of a signal waveform obtained from a 0.008 -mm-deep groove in the test material using the method according to the present invention.

FIG. 9 shows the signal obtained from the tape used to record the leakage flux from the 1.15 -mm groove, FIG. 10 shows the signal from the 0.2 -mm groove and FIG. 11 shows the signal from the 0.008 -mm groove. Each division along the horizontal axis of the graphs represents a distance of 0.093494 mm. In the graphs $H_1$ and $H_2$ are maximum and minimum values corresponding to the depth of the grooves and W denotes surface distance corresponding to the width of the grooves. Thus, the width as well as the depth of each groove can be determined from an analysis of the signal wave forms. For reference, the width of the groove of FIG. 9 is 0.411374 mm, that of the FIG. 10 groove is 0.0402024 mm and that of the FIG. 11 groove is 0.0691855 mm.

As shown by FIG. 11, with the method of this invention a flaw can be reliably detected that is only 0.008 mm deep, whereas a flaw that size cannot be detected with the conventional magnetic tape method of flaw detection.

Figure 12:
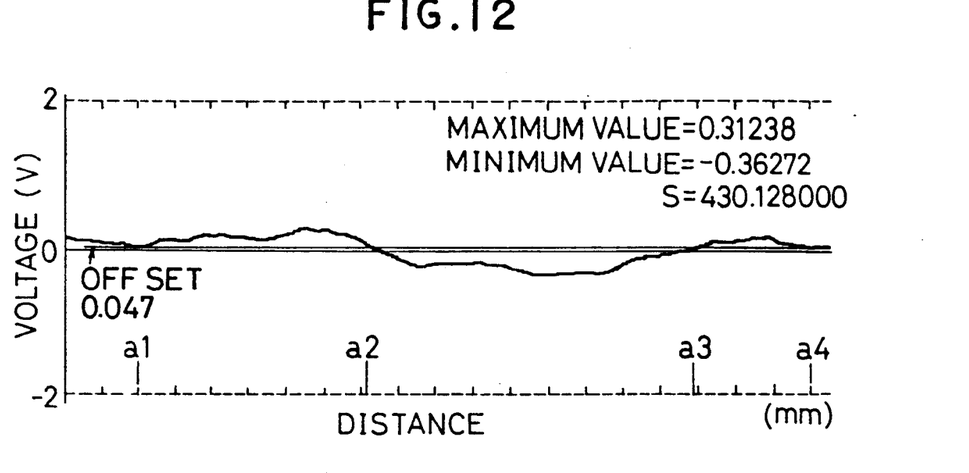
FIG. 12 is a graph showing the waveform of a signal obtained using SM 50 as the magnetic material.
Figure 13:
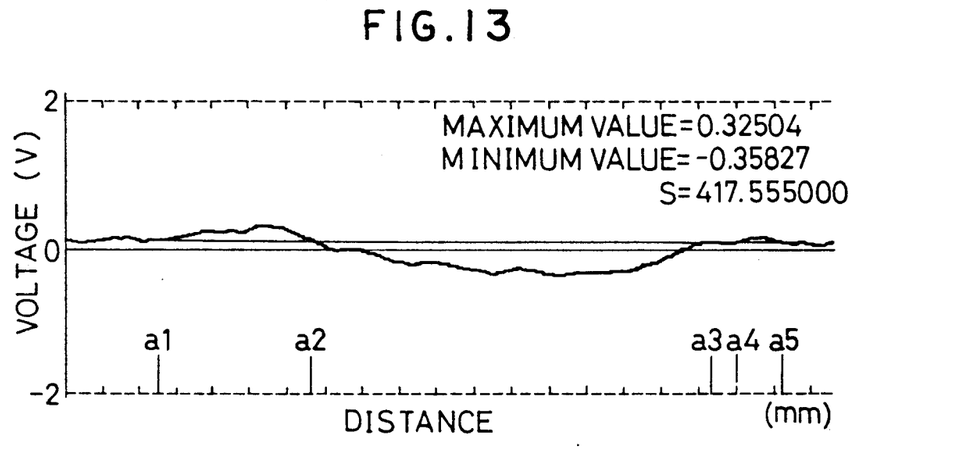
FIG. 13 is a graph showing the waveform of a signal obtained using SPCC as the magnetic material.

Next, SM 50 and a SPCC steel sheet 0.5 mm thick conforming to JIS standards were used as the test material in which a groove 3.2 mm deep was formed and the material was magnetized by the same procedure as the one described above, using a magnetization current of 9 amps and a lift-off of 0.2 mm. FIG. 12 shows the signal waveform obtained from the groove in the SM 50 and FIG. 13 shows the signal waveform obtained from the groove in the SPCC. The groove of FIG. 12 is 0.400154 mm wide and that of FIG. 13 is 0.435149 mm wide.

Figure 14:
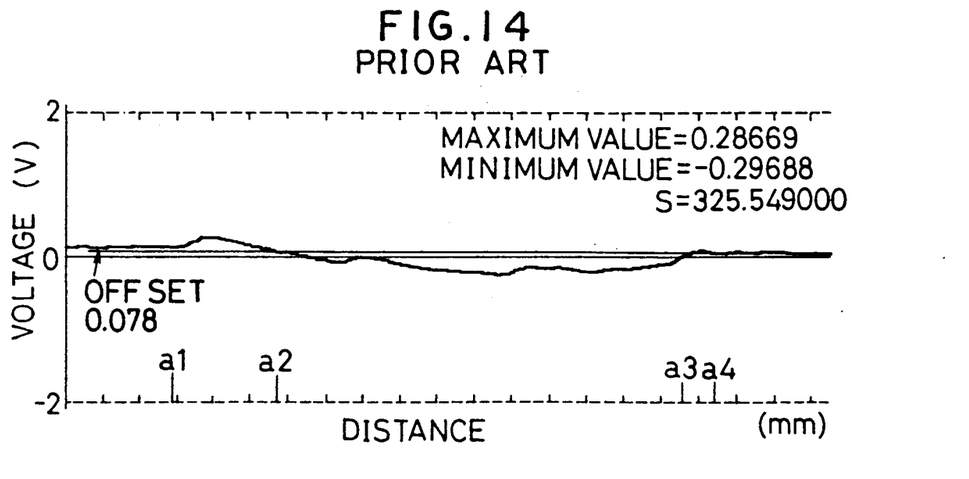
FIG. 14 is a graph showing the waveform of a signal obtained using a conventional leakage flux flaw detection method.

For the purpose of comparison, identical test materials were prepared to which magnetic tape was adhered and these samples were magnetized using a conventional method. The signal waveform obtained from these (in which the groove is 0.415113 mm wide) is shown in FIG. 14.

A simple comparison of maximum and minimum values shows that compared to the conventional method the method according to the present invention produces larger signal values. To show that overall the signals are larger when variance is excluded, a comparison of the total area S enclosed above and below the offset line produced respective approximate figures of 430, 417 and 325. (In the graphs $a_1$, $a_2$, $a_3$, $a_4$ and $a_5$ indicate the end points of the integral.)

Figure 15:
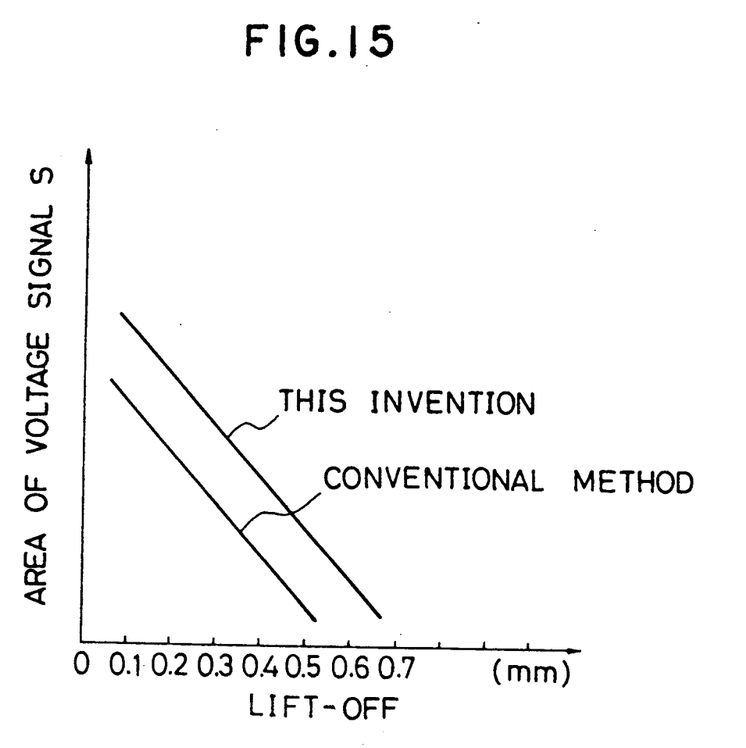
FIG. 15 is a graphic comparison of the relationship between lift-off and signal amplitude in the case of a conventional leakage flux flaw detection method and the method of this invention.

The amplitude of the signals (enclosed area of the voltage signal S) obtained by the method of the present invention and the conventional method were compared using the same lift-off for the same flaw (groove). This produced the graph of FIG. 15 showing the general relationship between lift-off and area S, which shows that, compared to the conventional method, flaw detection with the method of the present invention is possible at a larger lift-off.

Figure 16:
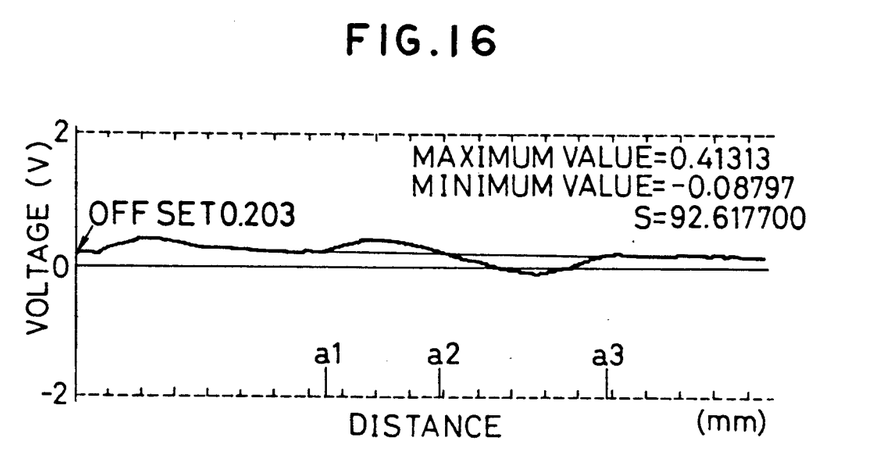
FIG. 16 is a graph showing the waveform of a signal obtained from a flaw in amorphous material in accordance with the present invention.

FIG. 16 shows the waveform of a signal detected from a flaw in a very thin amorphous material. A groove was formed to a depth of 0.23 mm in 0.23-mm iron-system amorphous film, i.e., the groove penetrated to the lower surface of the film. The amorphous film was arranged on the steel sheet material, from which it was separated by a 0.2-mm sheet of vinyl chloride. The amorphous film was then overlaid with magnetic tape, followed by a layer of 0.2-mm vinyl chloride and a 0.5-mm layer of steel sheet. The amorphous film was then magnetized in a magnetizer at a magnetization current of 10 amps. As shown by the above graph, the flaw can be detected even when the material of the test sample is very thin.

Thus, in accordance with the present invention, flaw detection can be automated and recorded and objective, quantitative evaluations are possible as well as evaluations based on changes over time, and it also enables the detection of very small flaws and of flaws in very thin materials and materials which are coated. This gives it a high degree of utility in non-destructive testing for surface flaws and flaws in welded structures and the like.

What is claimed is:

1. A leakage flux flaw detection method comprising: placing a magnetic recording material on a test surface of a test material; providing a layer of non-magnetic material on the magnetic recording material; providing a layer of ferromagnetic material on the layer of non-magnetic material, magnetizing the test material and recording leakage flux from the test material on the magnetic recording material.

2. A flaw detection method according to claim 1 wherein the non-magnetic layer is a high polymer film.

3. A flaw detection method according to claim 2 wherein the polymer film is vinyl chloride film.

4. A flaw detection method according to claim 1 wherein the ferromagnetic layer includes a sheet of a high polymer having magnetic properties.

5. A leakage flux flaw detection apparatus comprising:
a magnetic recording material one surface of which is in contact with a test surface of a test material;
an auxiliary recording member with a ferromagnetic layer and a non-magnetic layer arranged one on the other so that the non-magnetic layer is in contact with the magnetic recording layer;
and a magnetizer for magnetizing the test material.

6. A flaw detection apparatus according to claim 5 wherein the non-magnetic layer is a film of a high polymer material.

7. A flaw detection apparatus according to claim 5 wherein the auxiliary recording member is movably supported by the magnetizer.

8. A leakage flux flaw detection apparatus comprising:
a magnetic recording material one surface of which is in contact with a test surface of a test material;
a non-magnetic layer provided on the second surface of the magnetic recording material;
a ferromagnetic layer provided on the non-magnetic layer; and
a magnetizer for magnetizing the test material.

9. A flaw detection apparatus according to claim 8 wherein the non-magnetic layer is a film of a high polymer material.

10. A flaw detection apparatus according to claim 8 wherein the ferromagnetic layer is a sheet of steel.

11. A flaw detection method according to claim 1, which further comprises providing a second ferromagnetic layer on a surface of the test material opposite to the test surface via a second non-magnetic layer.

12. A flaw detection apparatus according to claim 8, wherein the magnetic recording material consists of a magnetic layer constituting the one surface of said magnetic recording material and a non-magnetic layer constituting the second surface of the non-magnetic layer.

13. A flaw detection apparatus according to claim 8, further comprising a second ferromagnetic layer provided on a surface of the test material opposite to the test surface via a second non-magnetic layer.

* * * * *

UNITED STATES PATENT AND TRADEMARK OFFICE
CERTIFICATE OF CORRECTION

PATENT NO. : 5,008,620
DATED : April 16, 1991
INVENTOR(S) : Katusnobu Nonaka et al.

It is certified that error appears in the above-identified patent and that said Letters Patent is hereby corrected as shown below:

On the title page, item [73]:
   The Assignee is incorrect, should be, --Agency of Industrial Science & Technology, Ministry of International Trade & Industry, Tokyo, Japan--.

Signed and Sealed this

Sixth Day of October, 1992

*Attest:*

DOUGLAS B. COMER

*Attesting Officer*      *Acting Commissioner of Patents and Trademarks*